United States Patent
Biedermann et al.

(10) Patent No.: US 10,258,397 B2
(45) Date of Patent: Apr. 16, 2019

(54) BONE ANCHOR AND BONE ANCHORING ASSEMBLY COMPRISING THE SAME

(71) Applicant: BIEDERMANN TECHNOLOGIES GMBH & CO. KG, Donaueschingen (DE)

(72) Inventors: Lutz Biedermann, VS-Villingen (DE); Markku Biedermann, Miami, FL (US); José Santiago-Anadón, Miami, FL (US)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/888,813

(22) Filed: Feb. 5, 2018

(65) Prior Publication Data

US 2018/0256230 A1    Sep. 13, 2018

Related U.S. Application Data

(63) Continuation of application No. 14/542,476, filed on Nov. 14, 2014, now Pat. No. 9,913,674.
(Continued)

(51) Int. Cl.
*A61B 17/84* (2006.01)
*A61B 17/68* (2006.01)
(Continued)

(52) U.S. Cl.
CPC .......... *A61B 17/846* (2013.01); *A61B 17/685* (2013.01); *A61B 17/8042* (2013.01);
(Continued)

(58) Field of Classification Search
CPC .............. A61B 17/8655; A61B 17/844; A61B 17/8038; A61B 17/846
See application file for complete search history.

(56) References Cited

U.S. PATENT DOCUMENTS

| 3,579,831 A | 5/1971 | Stevens et al. |
|---|---|---|
| 3,955,280 A | 5/1976 | Sneer |

(Continued)

FOREIGN PATENT DOCUMENTS

| EP | 1 658 816 A1 | 5/2006 |
|---|---|---|
| EP | 2 151 213 A1 | 2/2010 |

(Continued)

OTHER PUBLICATIONS

European Search Report for corresponding European Application No. 14153526.0 in the name of Biedermann Technologies GmbH & Co. KG, European Search Report dated Mar. 24, 2014 and dated Apr. 2, 2014 (6 pgs.).

(Continued)

*Primary Examiner* — Andrew Yang
(74) *Attorney, Agent, or Firm* — Lewis Roca Rothgerber Christie LLP

(57) ABSTRACT

A bone anchor includes: a main body defining a longitudinal axis and including a head; at least one insertion hole which extends from a first opening formed in the head to a second opening formed in the main body, the at least one insertion hole having an axis which is arranged to be inclined with respect to the longitudinal axis of the main body at an angle, and the insertion hole being configured to receive and guide therethrough a pin-shaped element to be anchored within a bone or bone fragment; and a locking device configured to lock the position of the pin-shaped element inserted within the at least one insertion hole in an axial direction.

22 Claims, 17 Drawing Sheets

Related U.S. Application Data

(60) Provisional application No. 61/904,399, filed on Nov. 14, 2013.

(51) Int. Cl.
    *A61B 17/80*     (2006.01)
    *A61B 17/86*     (2006.01)
    *A61B 17/72*     (2006.01)

(52) U.S. Cl.
    CPC ........ *A61B 17/8057* (2013.01); *A61B 17/844* (2013.01); *A61B 17/864* (2013.01); *A61B 17/8685* (2013.01); *A61B 17/686* (2013.01); *A61B 17/7266* (2013.01); *A61B 17/848* (2013.01); *A61B 17/8615* (2013.01); *A61B 17/8625* (2013.01); *A61B 17/8635* (2013.01); *A61B 2017/8655* (2013.01)

(56) References Cited

U.S. PATENT DOCUMENTS

| | | |
|---|---|---|
| 4,754,749 A | 7/1988 | Tsou |
| 5,984,681 A | 11/1999 | Huang |
| 8,333,591 B2 | 12/2012 | Zhao |
| 9,060,808 B2 | 6/2015 | Overes et al. |
| 2002/0022843 A1 | 2/2002 | Michelson |
| 2004/0193157 A1 | 9/2004 | Falahee |
| 2006/0111720 A1 | 5/2006 | Luca |
| 2010/0145397 A1 | 6/2010 | Overes et al. |
| 2011/0098747 A1 | 4/2011 | Donner et al. |
| 2013/0030478 A1 | 1/2013 | Rodriguez |
| 2013/0053891 A1 | 2/2013 | Hawkins et al. |

FOREIGN PATENT DOCUMENTS

| | | |
|---|---|---|
| JP | 2001-252283 A | 9/2001 |
| JP | 2009-527277 A | 7/2009 |
| JP | 2012-510875 A | 5/2012 |
| WO | WO 2005/092219 A1 | 10/2005 |
| WO | WO 2007/095428 A1 | 8/2007 |
| WO | WO 2010/065855 A1 | 6/2010 |
| WO | WO 2013/033584 A2 | 3/2013 |

OTHER PUBLICATIONS

Extended European Search Report for corresponding European Application No. 14153526.0 in the name of Biedermann Technologies GmbH & Co. KG, European Search Report dated Jun. 27, 2014 and dated Jul. 10, 2014 (11 pgs.).

JP OA dated Nov. 29, 2016 for Application No. 2014-228706 (6 pages) and English translation (9 pages).

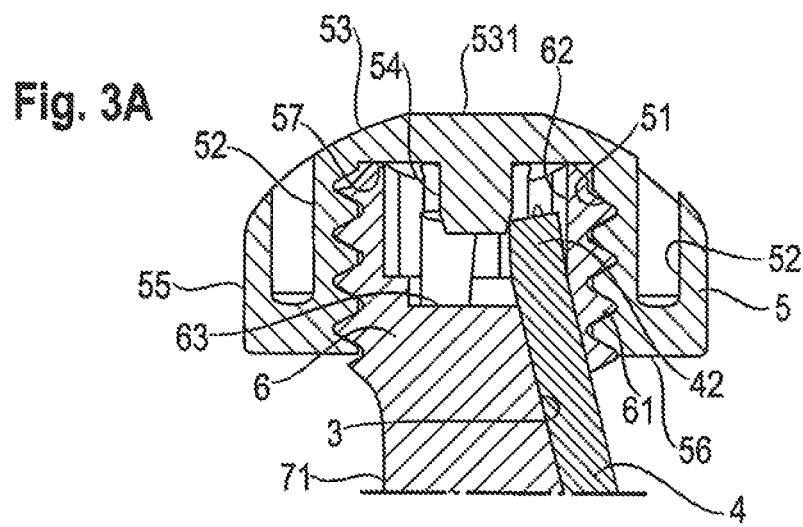
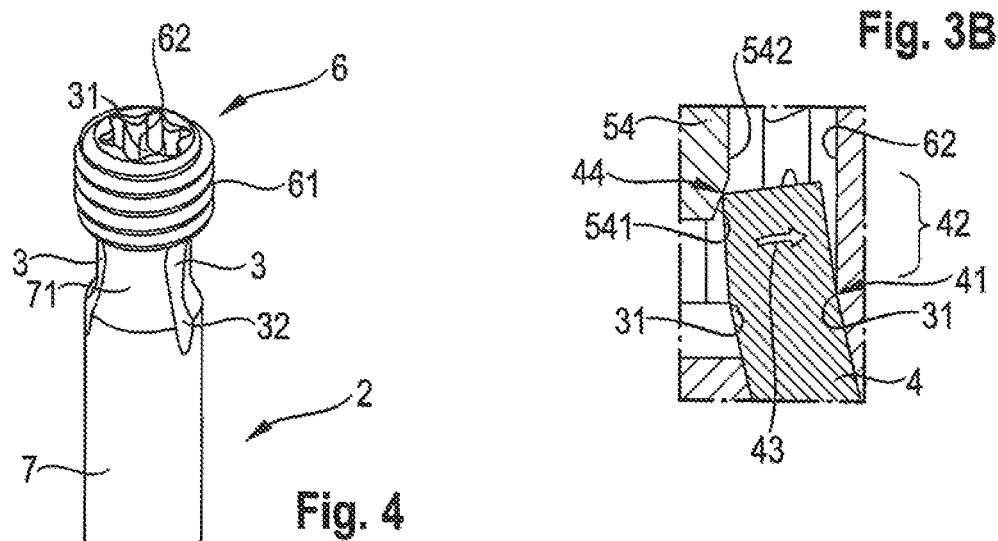
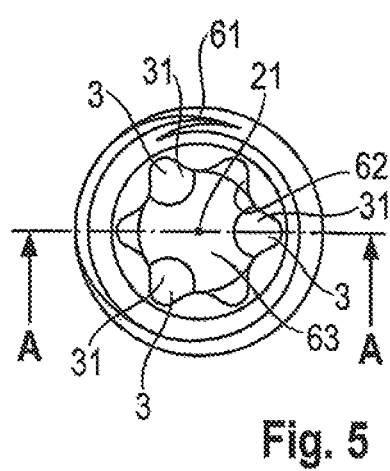

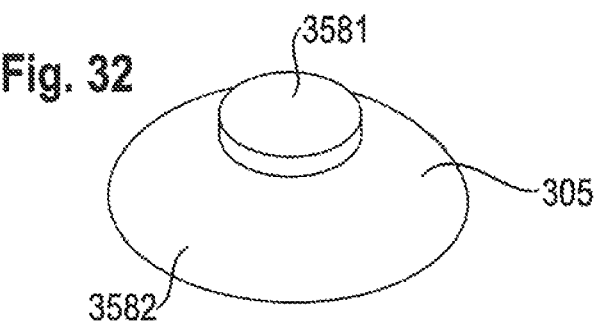
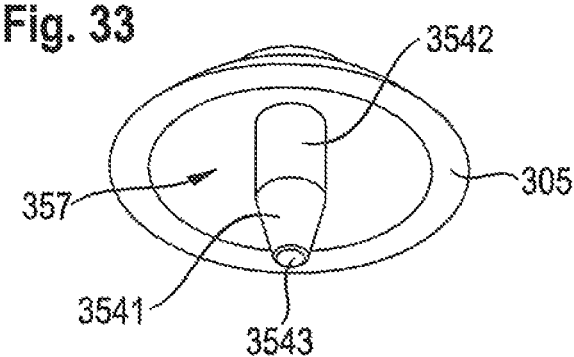
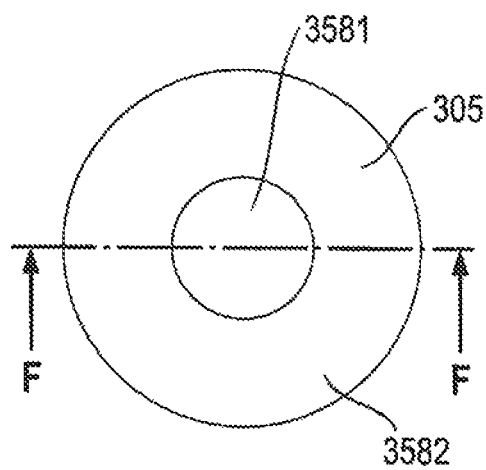
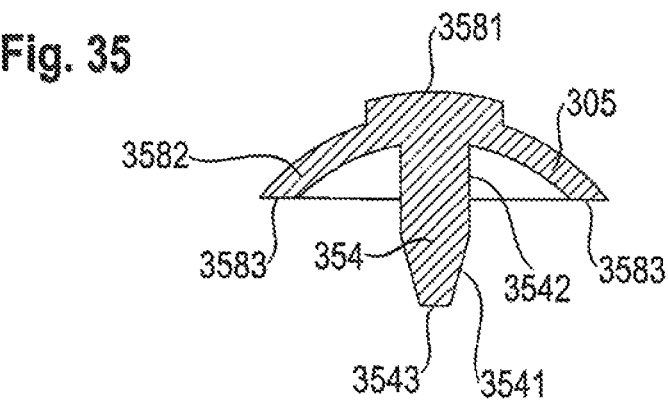

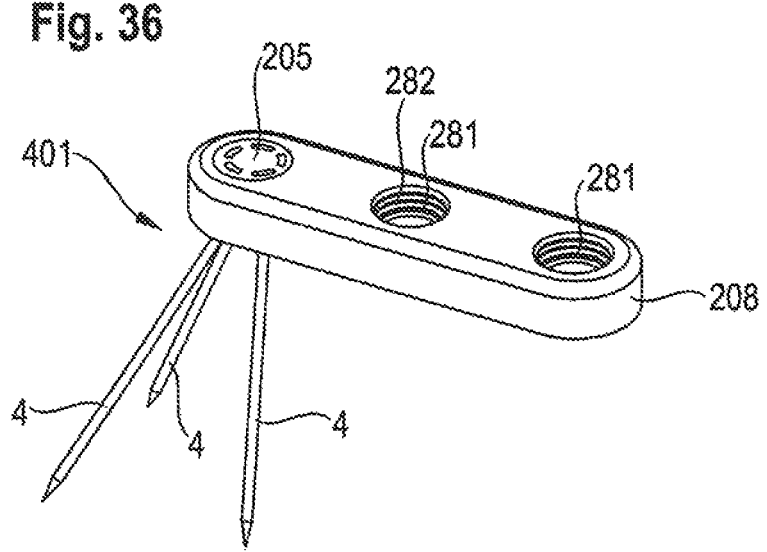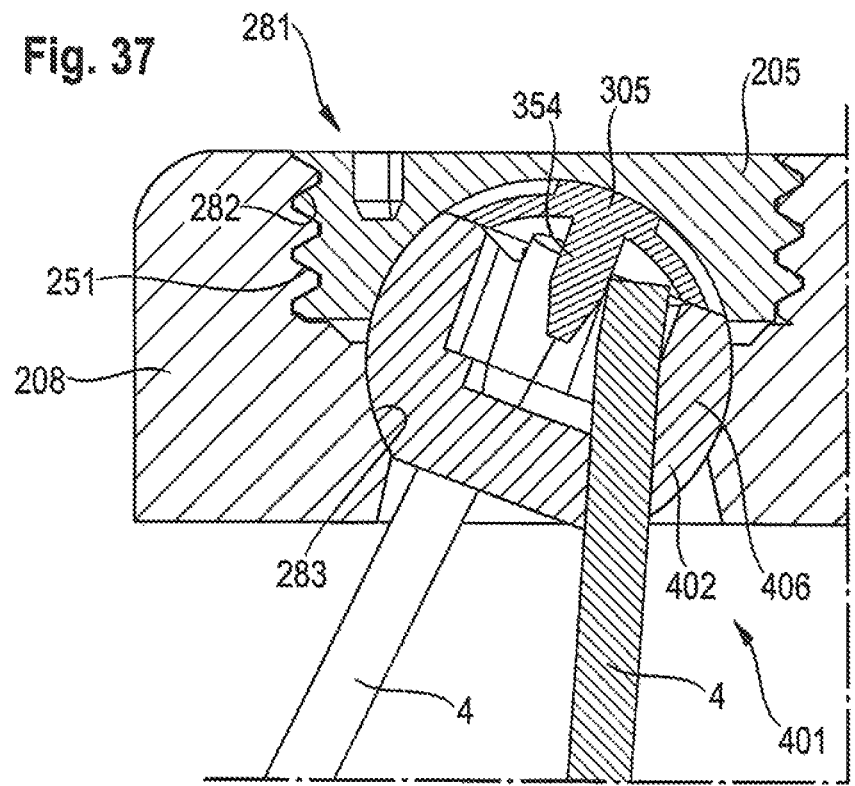

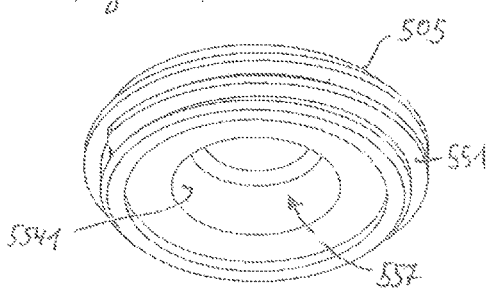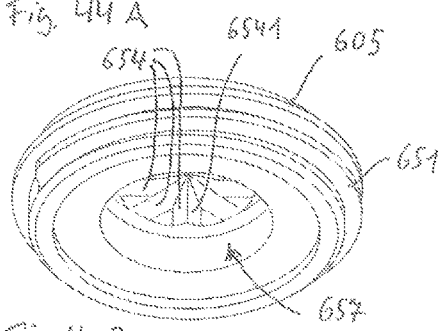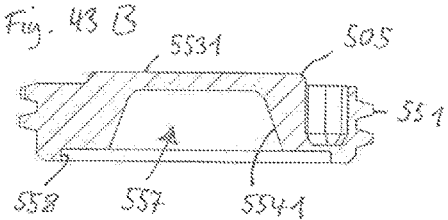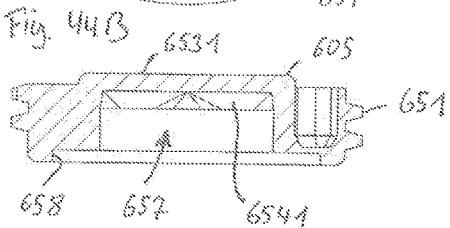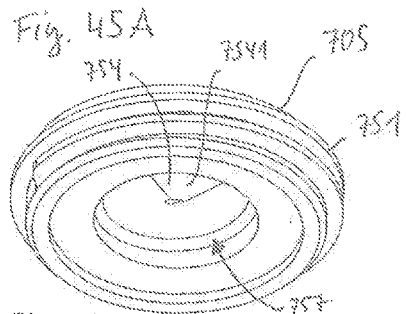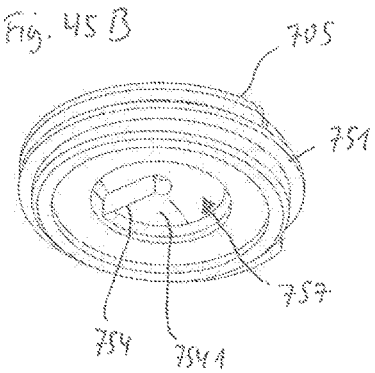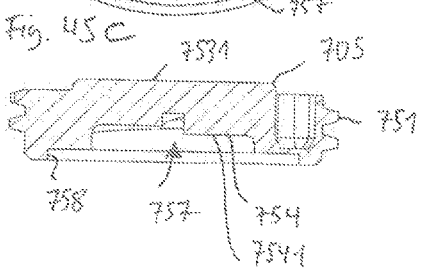

BONE ANCHOR AND BONE ANCHORING ASSEMBLY COMPRISING THE SAME

CROSS-REFERENCE TO RELATED APPLICATION

This application is a continuation of U.S. patent application Ser. No. 14/542,476, filed Nov. 14, 2014, which claims the benefit of U.S. Provisional Patent Application Ser. No. 61/904,399, filed on Nov. 14, 2013, the entire content of which is hereby incorporated by reference.

BACKGROUND

The present invention relates to a bone anchor for use in clinical surgery, for example in the treatment of traumatic fractures caused by osteoporosis of bones, among others. The bone anchor has a main body with a head. One or more insertion holes extend from a first opening formed in the head towards a second opening formed in the main body, for example in the head as well or in a shank, wherein the insertion hole has an axis that is generally inclined with regard to a longitudinal axis of the main body. The insertion hole is configured to receive and guide therethrough a pin-shaped element, such as for example a Kirschner-wire, which is to be anchored within the bone or bone fragment under concern.

Such pin-shaped elements may help in preventing a loosening of a bone anchor formed as a bone screw from a bore hole formed in the bone. Due to the inclination of the pin-shaped element with respect to the longitudinal axis of the bone anchor, the head is rotationally fixed and may remain in its position once the pin-shaped elements are inserted through the insertion holes and further introduced into the adjacent bone material.

One example is described in document US 2006/0111720 A1. The surgical screw being disclosed is configured to attach a blocking plate to a bone. The screw comprises two holes inclined with respect to the screw. Each hole receives a surgical nail made of a stainless metal. The inclined holes extend from a hexagonal engagement portion formed in the screw head and open into a transition region between the spherical head and a neck portion of the threaded stem. The surgical nail is of the Kirschner-type. The surgical nail solves spontaneous loosening problems of the surgical screw.

The use of inclined pins is also known from a dental implant described in U.S. Pat. No. 3,579,831. Two pins are guided through inclined bores extending through a shank section in order to stabilize the rotational position of the implant such as to retain the screw reliably in the bone.

Another dental implant is disclosed in U.S. Pat. No. 5,984,681. The implant tapers towards a lower terminal end and comprises an access opening for engagement with a false tooth at its proximal end. A through bore extends from the bottom of the access opening in an inclined fashion with respect to the longitudinal access of the implant. An anchoring pin or screw is received therein which has a threaded self-tapping portion for insertion into the alveolar bone of a patient.

In each of the above described cases, while the implant or bone screw is reliably maintained or stabilized within the adjacent bone material due to the inclined nails, wires or pins, there may still arise a problem that such nails, wires or pins itself may loosen from the bone material in which they are anchored. They may thus lose their capacity of stabilizing or retaining the main body of the respective implant or bone screw.

This problem may particularly become important in cases where the pins, nails or wires function to reposition or fixate fractures of bones or bone fragments, or where these are applied in the arthrodesis of smaller joints, for example.

SUMMARY

According to aspects of embodiments of the present invention, a bone anchor, and a bone anchoring assembly comprising a bone anchor have increased reliability and stability with regard to pin-shaped elements guided through inclined insertion holes of respective bone anchors to be anchored in bones or bone fragments.

Advantageous aspects and features of embodiments of the present invention are described herein with respect to some exemplary embodiments and are set forth in the claims.

A bone anchor according to embodiments of the present invention has a main body which may at least comprise a head. At least one insertion hole extends in an inclined fashion with regard to the longitudinal axis of the main body from a first opening at the head towards a second opening at the main body. The insertion hole is configured to receive and guide therethrough a pin-shaped element, which may be an anchoring pin, a nail, a wire, such as a Kirschner-wire, etc.

A corresponding locking device allows locking or clamping of the pin-shaped element. It is further provided to the bone anchor and is configured to lock the position of the at least one pin-shaped element within the insertion hole. As a consequence, when the locking device is provided to the bone anchor, the pin-shaped element is fixed in position and cannot move in or out of the insertion hole in an axial direction and is thus reliably retained therein.

According to embodiments, the locking device may be formed as a cap. The cap-like locking device is attached to the head. The cap may have a surface which interacts with the pin-shaped element received and guided through the insertion hole. At this instance, the interaction between the locking device, or cap, with the pin-shaped element received in the insertion hole may be in a friction-fit fashion and/or in a manner of closing an extraction path. Each of the alternatives cited above is comprised by the subject matter as claimed herein.

The friction-fit locking, i.e., locking by clamping, becomes applicable if the surface of the locking device or cap is configured to exert some pressure force, or clamping force, onto the pin-shaped element during attachment of the locking device.

Closing of an extraction path may simply be effected by attaching a cap that closes a path or space (for example, along an axis of the insertion hole) through which the pin-shaped element would move out when it loosens. In the exemplary embodiments discussed below, the engagement portions of bone anchors contain, or even simultaneously represent, openings of insertion holes. Such engagement portions are entirely closed by a cap as an example, irrespective of whether clamping is effected by further specific structures provided at the locking means.

The expression "attached" with regard to the locking device with respect to the head as used with respect to some embodiments described herein includes a fixed coupling between both parts using, for example, respective threads cooperating with each other. Such expression "attached" also encompasses embodiments wherein the locking device is simply connected or pressed onto the head wherein the connection is maintained by other means external or internal to the bone anchor or bone anchoring assembly.

It is not necessary that the locking device directly contacts the head. It is also possible that intermediate parts between the locking device and the pin-shaped element received in the insertion hole lead to the locking of the same.

With regard to the expression "main body" as used herein, it is contemplated that this expression may refer to a monolithic part as well as to a multiple piece assembly, wherein, for example, the main body comprises a head, a shank and a tip, and these parts are provided as separate pieces connectable to each other. In one embodiment, the main body comprises a head without a shank or a tip.

BRIEF DESCRIPTION OF THE DRAWINGS

For a better understanding of the bone anchor as described herein, features and aspects will become apparent by a more detailed description of embodiments taken in conjunction with the drawings, wherein:

FIG. 3A shows a cross-sectional view of a head portion assembled with a locking device and a pin-shaped element in the bone anchor according to the first embodiment;

FIG. 3B shows an enlarged view of a protruding portion of the pin-shaped element as shown in FIG. 3A;

FIG. 4 shows a perspective view of a main body of the bone anchor according to the first embodiment;

FIG. 5 shows a top view of a head of the bone anchor shown in FIG. 4 according to the first embodiment;

FIG. 32 shows a top perspective view of an additional cap of a bone anchoring assembly according to the fourth embodiment;

FIG. 33 shows a bottom perspective view of an additional cap of a bone anchoring assembly according to the fourth embodiment;

FIG. 34 shows a top view of an additional cap of the bone anchoring assembly according to the fourth embodiment;

FIG. 35 shows a cross-sectional view of the additional cap of the bone anchoring assembly according to the fourth embodiment along the line F-F shown in FIG. 34;

FIG. 36 shows a perspective view of a bone anchoring assembly with a bone anchor according to a fifth embodiment;

FIG. 37 shows a cross-sectional view of the bone anchoring assembly according to FIG. 36;

FIG. 43A shows a bottom perspective view of a locking device of the bone anchoring assembly according to a first modification of the second embodiment;

FIG. 43B shows a cross-sectional view of the locking device of the bone anchoring assembly according to the first modification of the second embodiment shown in FIG. 43A;

FIG. 44A shows a bottom perspective view of a locking device of the bone anchoring assembly according to a second modification of the second embodiment;

FIG. 44B shows a cross-sectional view of the locking device of the bone anchoring assembly according to the second modification of the second embodiment shown in FIG. 44A;

FIG. 45A shows a bottom perspective view of a locking device of the bone anchoring assembly according to a third modification of the second embodiment;

FIG. 45B shows a bottom perspective view of the locking device of the bone anchoring assembly according to the third modification of the second embodiment from a different view point than that in FIG. 45A, wherein a ramp becomes clearly visible;

FIG. 45C shows a cross-sectional view of the locking device of the bone anchoring assembly according to the third modification of the second embodiment shown in FIG. 45A;

DETAILED DESCRIPTION

Figure 1:
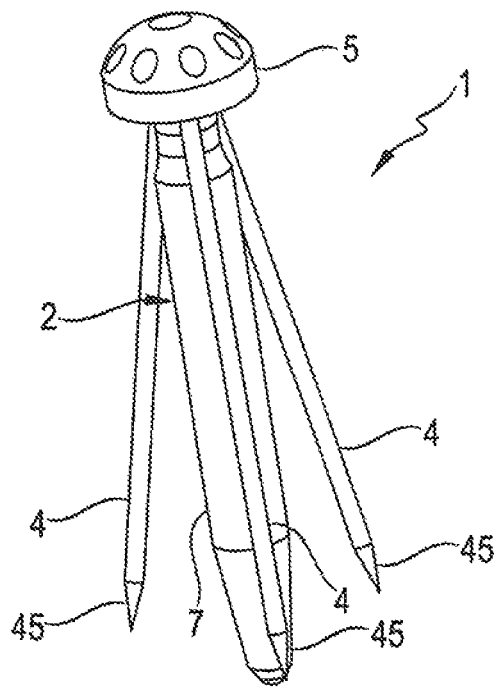
FIG. 1 shows a perspective view of a bone anchor according to a first embodiment in a state assembled together with pin-shaped elements.
Figure 2:
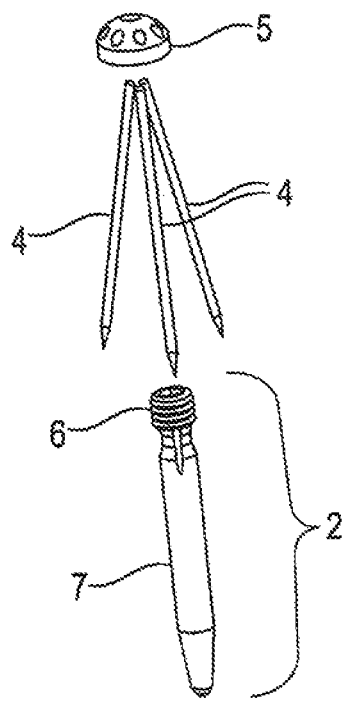
FIG. 2 shows an exploded view of the bone anchor of FIG. 1.

A first embodiment of a bone anchor as proposed herein is illustrated in conjunction with FIGS. 1-11. An overview of the bone anchor 1 according to the first embodiment becomes apparent from FIGS. 1 and 2. The bone anchor 1 comprises a main body 2 and a locking device 5, which is formed as a cap and will be described in detail further below. The main body 2 is formed as a monolithic piece according to this embodiment and comprises a head 6 and a shank 7.

Three pin-shaped elements 4 extend from the head 6. More specifically, as shown in FIG. 4 three respective insertion holes 3 are formed at a head portion of the main body 2 which may each receive one of the pin-shaped elements 4, from which the pin-shaped elements 4 protrude outwards in an inclined fashion with respect to the shank 7. The head 6 further comprises an outer thread 61, for example a metric thread, and an engagement portion 62 for engagement by an external tool (not shown), for example, a star drive (e.g., Torx), hex socket (e.g., Allen key), etc. In the present embodiment, a star (e.g., Torx) screw drive type is used for the engagement portion 62. As can be seen in more detail from FIG. 3A, the engagement portion 62 of the head 6 has a bottom face 63, from which three first openings 31 of the respective insertion holes 3 extend.

Figure 11:
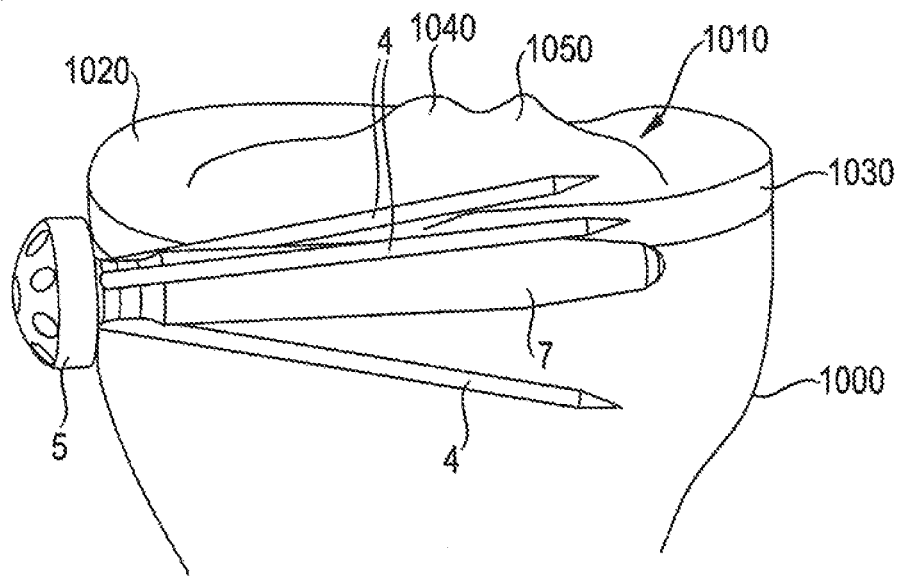
FIG. 11 shows a perspective view of the bone anchor according to the first embodiment in operation implanted adjacent to the tibia plateau.

The pin-shaped elements 4 are received in and guided through the insertion holes 3 and slightly protrude with an end portion 42 from the first openings 31 into the inner space of the engagement portion 62. On the other side, as shown in FIG. 1 or FIG. 11, the pin-shaped elements 4 protrude out of a second opening 32 of the insertion hole 3 with a length substantially comparable to that of the main body 2. Sharp tips 45 of the pin-shaped elements 4 extend up to a depth of a tapering portion 72 adjacent to the tip 73 of the shank 7, in the installed state of the pin-shaped elements 4.

The pin-shaped elements 4 are preferably made of stainless steel or titanium or of other biocompatible materials. Due to a diameter of less than 3 mm, for example, and preferably less than 2 mm, and more preferably less than 1 mm, the pin-shaped elements 4 may be bent. Minimum diameters of the pin-shaped elements 4 may be 0.5 mm. However, the insertion holes 3 are preferably straight throughout the embodiments described herein. Nevertheless, it is possible the holes may also be curved, in particular slightly curved, with a comparatively small amount of friction, as compared with the clamping friction caused by the structure of the locking device 5. This applies also to the other embodiments described herein.

The diameters of the insertion holes 3 and the pin-shaped elements 4 also correspond to each other such as to allow insertion and guiding through of the pin-shaped elements 4 with reduced friction during assembly.

The shank 7 further has, in addition to the rounded tip 73 and the adjacent tapering portion 72, an almost cylindrical, threadless main portion 74 as well as a neck portion 71, which is positioned opposite to the tapering portion 72 and is provided adjacent to the head 6. The second openings 32 of the three insertion holes 3 are substantially provided at such neck portion 71.

As can be seen in FIG. 5, which shows a top view onto the head 6 of the main body 2, the three first openings 31 are each provided in one of the six lateral recesses of the star (e.g., Torx) engagement portion. In this manner, the three insertion holes 3 are symmetrically arranged around a central longitudinal axis 21 of the main body 2 (in FIG. 5 the longitudinal axis is perpendicular to the plane of the drawing). Due to this arrangement, the free end portions 42 of the pin-shaped elements 4 which protrude into the inner space of the engagement portion 62 may advantageously be retained fully within that space while maintaining a sufficient distance towards the central longitudinal axis 21.

Figure 6:
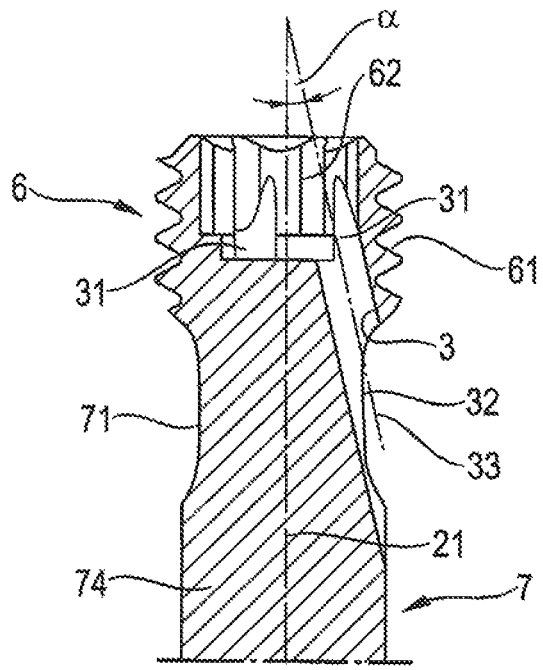
FIG. 6 shows a cross-sectional view of a head portion of the main body of the bone anchor according to the first embodiment along the line A-A shown in FIG. 5.

FIG. 6 shows that a longitudinal axis 33 of the insertion hole 3 includes an angle α with the longitudinal axis 21 of the main body 2. In the present embodiment, a is around 15°, but any other suitable angle a ranging from 0° to 90° is encompassed by this or another embodiment of the invention. In the present embodiment, the neck portion 71 of the shank 7 has a narrowed diameter as compared with the head 6 as well as with the cylindrical main portion 74 of the shank 7. As a consequence, the second opening 32 may be closer to the head 6. A comparatively large distance of the first opening 31 from the central longitudinal axis 21 and the comparatively small distance of the second opening 32 from the central longitudinal axis 21 due to the narrowed neck portion 71 allow a small inclination angle a for the orientation of the pin-shaped elements 4 with respect to the longitudinal axis 21 of the main body 2. At the same time, the overall diameter of the main body including the shank 7 and head 6 is kept small.

Figure 7:
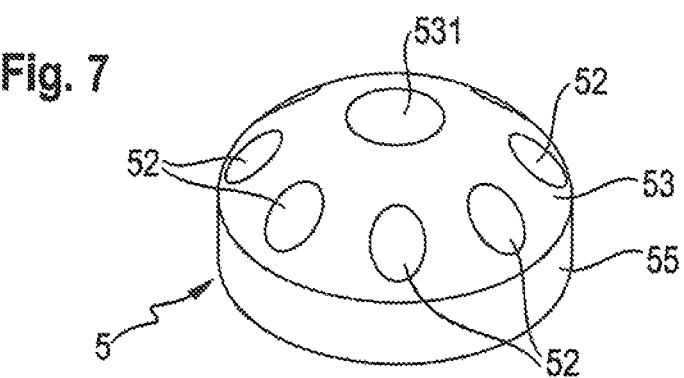
FIG. 7 shows a top perspective view of a locking device of the bone anchor according to the first embodiment.
Figure 8:
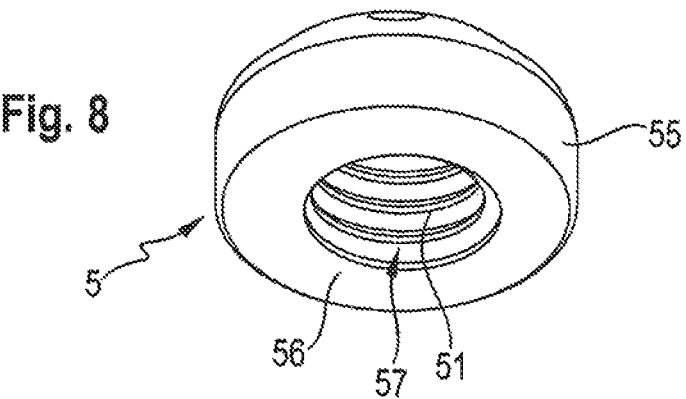
FIG. 8 shows a bottom perspective view of the locking device according to the first embodiment.
Figure 9:
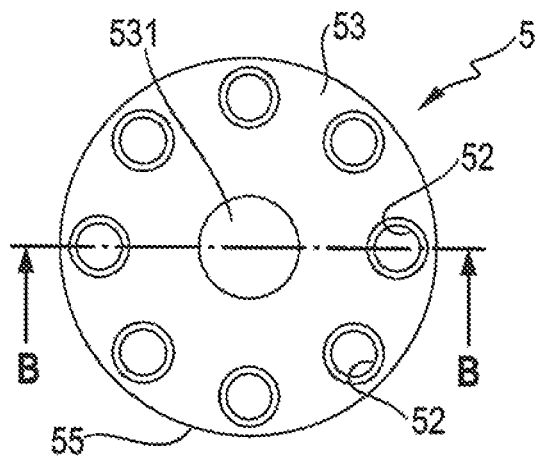
FIG. 9 shows a top view of the locking device according to the first embodiment.

The locking device 5 according to the first embodiment will be described with reference to FIGS. 7, 8 and FIG. 3A. The locking device 5 is attached to the head 6 via an inner thread 51, for example a metric thread, which is threaded onto outer thread 61 of the head 6. The locking device 5 is formed like a cap, which is attached to the head 6 such as to cover the same almost entirely from the top and lateral sides. The locking device 5 has an inner recess 57 in which the inner thread 51 is formed. Accordingly, the locking device 5 can be screwed onto the head 6.

The outer contour of the locking device 5 comprises a spherical segment shaped top face 53 having a central flat portion 531 and a generally cylindrical lateral face 55, and further an annular bottom face 56. Vertically extending holes 52 are formed in the spherical segment shaped top face 53, which allow, for example, access by an external tool for screwing the locking device 5 onto the head 6.

Figure 10:
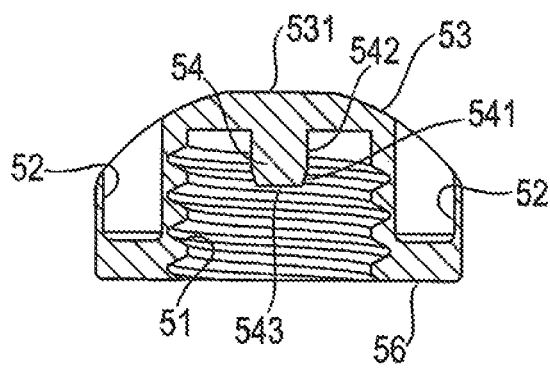
FIG. 10 shows a cross-sectional view of the locking device shown in FIG. 9 along the line B-B.

As can be seen in particular in FIG. 3A but in more detail in FIG. 10 (wherein the cross-sectional view of FIG. 10 is taken along the line B-B in FIG. 9), the locking device 5 includes a pin-like central projection 54 within the inner recess 57 extending or protruding from a top face of the inner recess 57. When the locking device 5 is screwed onto the head 6, the central projection 54 extends along and is aligned with the longitudinal axis 21 of the main body 2.

FIG. 3B shows an enlarged portion of FIG. 3A with respect to the central projection 54 and its interaction with the free end portion 42 of the pin-shaped element 4 which freely protrudes from the first opening 31 into the inner space of the engagement portion 62 of the head 6. The tip of the central projection 54 has the shape of a truncated cone including a conical wall surface 541, which extends from a substantially cylindrical base portion 542 of the projection 54.

When the cap-like locking device 5 is attached to the head 6, i.e., is screwed onto the head 6, the central projection 54 approaches the inner space of the engagement portion 62, wherein it occurs that the conical wall surface 541 contacts an upper edge portion 44 of the end portion 42 of the pin-shaped element 4. Due to its conical geometry the wall surface 541 is inclined with respect to the free end portion 42 and its upper edge 44. Thus, upon further advancement, an almost lateral pressure force is exerted by the projection 54 and the wall surface 541 onto the edge portion 44 and the end portion 42.

As a consequence, the free end portion 44 is laterally bent about point 41 (see FIG. 3B) which is formed by an edge of the first opening 31 of the insertion hole 3. Further screwing of the locking device 5 increases the pressure force and the displacement. A further bending 43 of the end portion 42 is the result. The bending 43 of the end portion 42 around edge point 41 of the first opening 31 leads to a locking of the pin-shaped element 4 within the insertion hole 3. This means that an upper portion of the pin-shaped element 4 including the end portion 42 is friction-fit within the head 6 of the bone anchor 1. Loosening of the pin-shaped element 4 towards a proximal direction (upper direction in FIG. 4) becomes impossible.

FIG. 11 shows a bone anchor 1 in use with pin-shaped elements 4 being implanted into the tibia 1000 beneath the tibea plateau 1010. Also indicated are the lateral meniscus 1020, the medial meniscus 1030, the anterior cruciate ligament 1040 and the posterior cruciate ligament 1050. The bone anchor 1 with pin-shaped elements 4 is implanted in this example to treat fractures or damages with regard to osteoporotic degenerations occurring at the tibia plateau 1010.

It may be noted that the shape and size of the central projection 54 of the locking device 5 which effects locking may deviate from the geometrical conditions shown with respect to the embodiments presented herein. The inclination of the wall surface that leads to a bending 43 depends upon and is thus to be realized with respect to the axis 33 of the insertion hole 3 along which the pin-shaped element is assumed to extend, such as to effect deflection and bending of the protruding end portion. The exact shape and inclination of the tapered or conical tip of the central projection may thus depend on the circumstances.

In an alternative embodiment, for example, it may also be conceived that the projection has no tapered or conical tip, but a radius of the central projection 54 varies around the azimuthal direction such that the end portions 42 of the pin-shaped elements 4 are alternately deflected and released with each turn of the locking device 5 when threading the same onto the head 6. The function is like a cam and a cam follower. Then, only a final rotary position of the locking device 5 needs to be such, that the end portions 42 are deflected in order to yield a locking of the pin-shaped elements 4. Marks provided at the locking device may indicate the correct rotary position.

Figure 12:
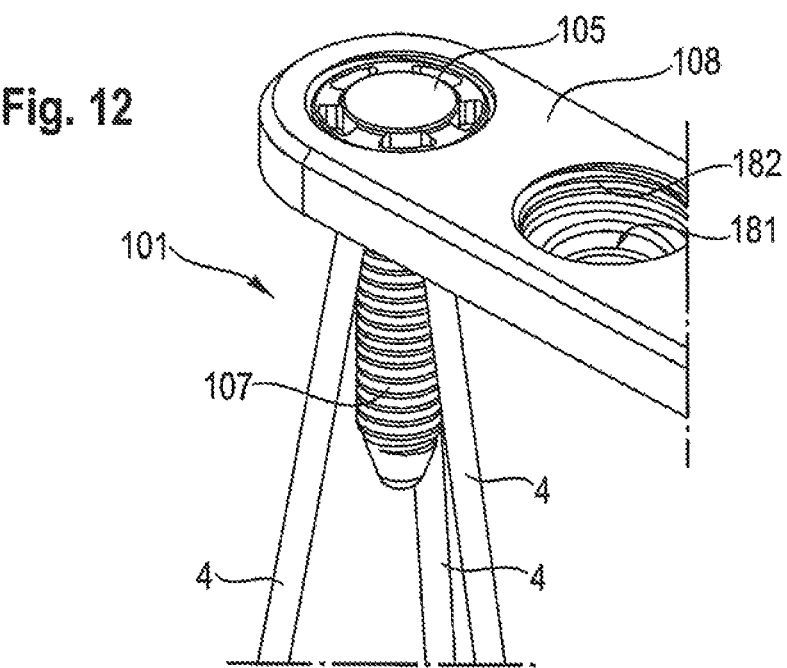
FIG. 12 shows a perspective view of a bone anchoring assembly with a bone anchor according to a second embodiment.
Figure 13:
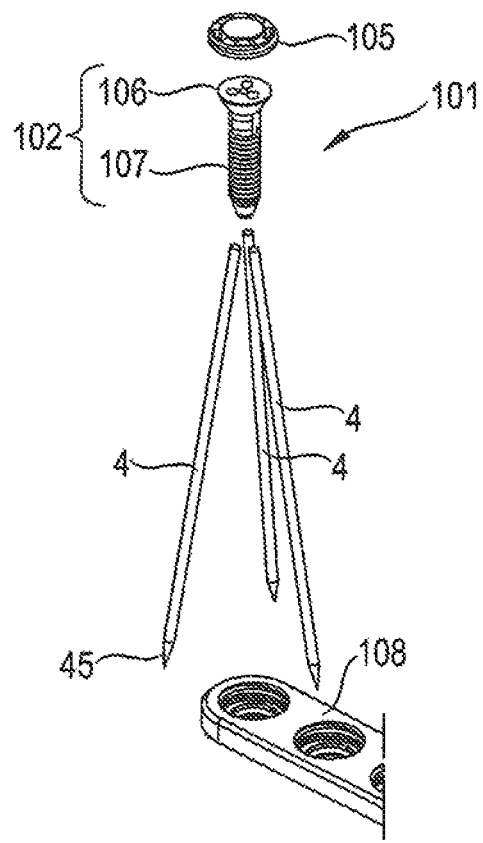
FIG. 13 shows an exploded view of the bone anchoring assembly of FIG. 12.

A second embodiment of a bone anchor will be described with reference to FIGS. 12 through 25. FIGS. 12 and 13 display an overview of a bone anchor 101 that is configured to be assembled with a bone plate 108. The bone plate 108 may, for example, receive two, three, or more of the bone anchors 101 in respective apertures 181, each of the bone anchors 101 configured to be anchored in bones or bone fragments, for example of the humerus bone, and then connected by the bone plate 108 to reposition and fixate the bones or fragments after a fracture.

The bone anchor 101 comprises a main body 102 including a head 106 and a shank 107, and a locking device 105 configured to be attached to the head 106. There are further provided three pin-shaped elements 4 which are inserted into respective insertion holes 103 (see FIGS. 14B or 18) and extend from second openings 132 formed in the head 106 and/or neck portion 171. As can be seen from FIG. 18, an axis 133 of the insertion hole 103 is inclined with respect to a longitudinal axis 121 of the main body 102.

Details of the main body 102 of the bone anchor 101 are explained with reference to FIGS. 15 through 18. The head 106 includes a planar upper surface 165, in which three first openings 131 for insertion the pin-shaped elements 4 are formed. The three first openings 131 are arranged in symmetrical manner with the same distance from the central longitudinal axis 121. A lower portion 166 of the head 106 is of substantially spherical segment shape, which corresponds to a respective spherical segment-shaped recess 183 formed in a lower portion of the aperture 181 of the bone plate 108 to receive the head 106 of the bone anchor 101. The head 106 further has an annular rim 167 protruding laterally beyond the upper edge of the lower portion 166. The rim 167 abuts on a shoulder above the lower portion in the aperture 181 of the bone plate 108. As a consequence of this structure, the bone anchor 107 has a predetermined orientation when being installed to the bone plate 108 as can be seen from FIG. 14A. In a central portion of the upper planar surface 165 of the head 106, a recess 164 is formed configured to receive a central projection 154 of the locking device 105 as will be discussed below.

The shank 107 comprises the neck portion 171 in which the second openings 132 of the insertion holes 103 are formed. The neck portion 171 is threadless wherein the second openings 132 due to their sharp inclination extend up to the adjacent threaded main portion 174 of the shank 107. The threaded main portion 174 is substantially cylindrical. The shank 107 has a tapered and rounded tip 172 at its distal end. In this embodiment, the neck portion 171 has substantially the same diameter as the cylindrical threaded main portion 174.

The locking device 105 will be explained with reference to FIGS. 19 through 22. The locking device 105 of the second embodiment has an outer thread 151 configured to cooperate with an inner thread 182 of an upper portion of the aperture 181. The locking device 105 has a substantially planar upper surface 1531 with five annularly distributed engagement holes 152, which may be engaged by an external tool (not shown) to screw-in the locking device 105 into the aperture 181 of the bone plate 108. As can be seen in the bottom view of FIG. 20, the locking device 105 has an inner recess 157 opening towards its bottom side, wherein a central projection 154 is provided which has a truncated cone shape towards its tip.

More specifically, the central projection 154 has a pin-shape with a cylindrical base portion 1542 and a conically shaped wall surface 1541 towards its tip, wherein the cone is truncated by a flat surface 1543. The truncated cone with flat surface 1543 is configured to be received by the central recess 164 formed in the planar upper surface 165 of the head 106 of the bone anchor 101, when the locking device 105 is attached to the head 106 to reliably align, hold and support projection 154 of the locking device 105 in the correct position.

Figure 14A:
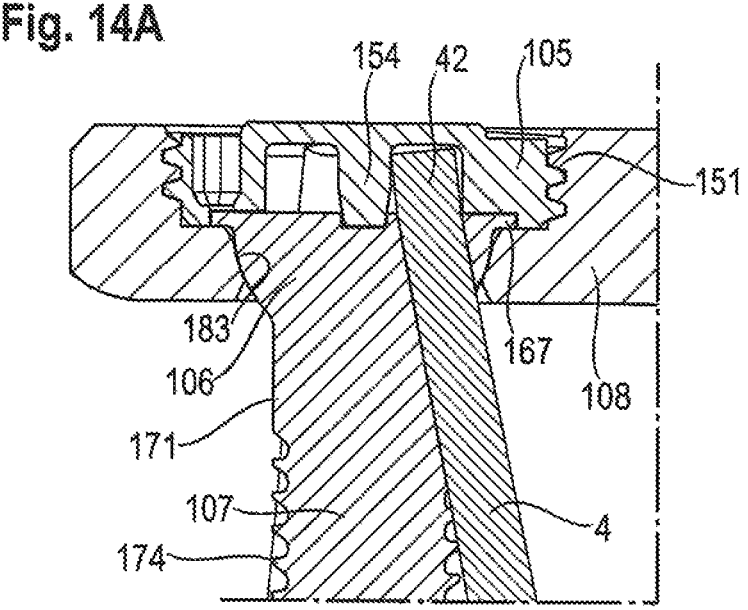
FIG. 14A shows a cross-sectional view of a head portion assembled to a bone plate of the bone anchoring assembly according to the second embodiment.
Figure 14B:
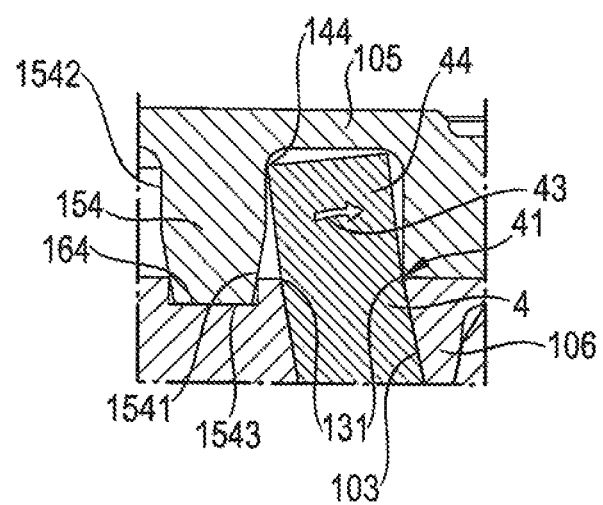
FIG. 14B shows an enlarged view of an end portion of the pin-shaped element assembled in an insertion hole as shown in FIG. 14A.
Figure 15:
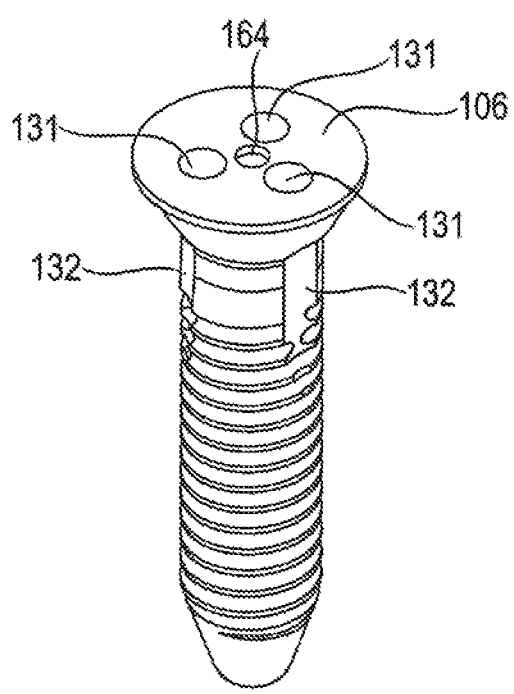
FIG. 15 shows a top perspective view of a main body of the bone anchoring assembly according to the second embodiment.
Figure 16:
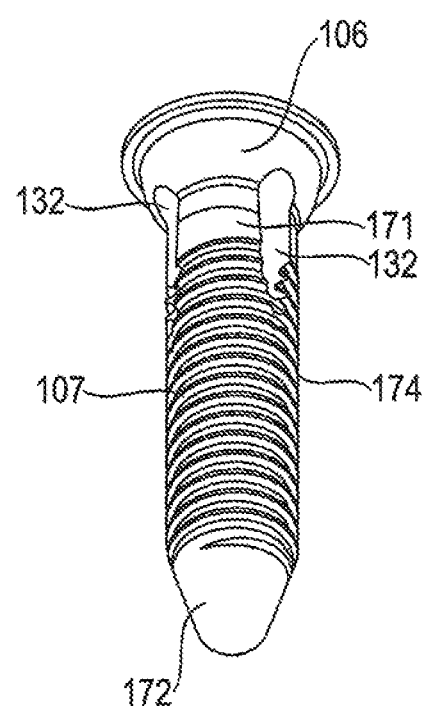
FIG. 16 shows a bottom perspective view of a main body of the bone anchoring assembly according to the second embodiment.
Figure 17:
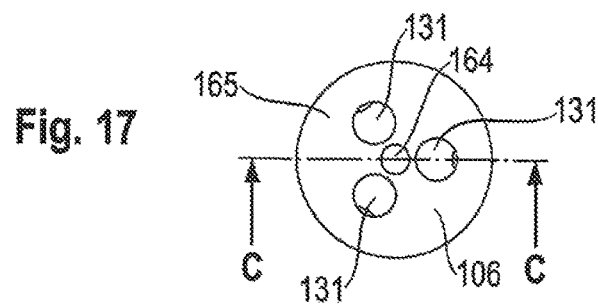
FIG. 17 shows a top view of a main body of the bone anchoring assembly of the second embodiment.
Figure 18:
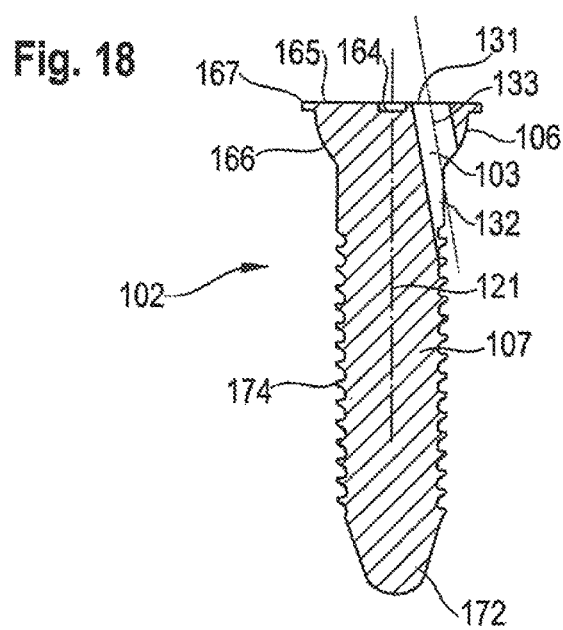
FIG. 18 shows a cross-sectional view of the main body of the bone anchoring assembly according to the second embodiment along the line C-C shown in FIG. 17.
Figure 19:
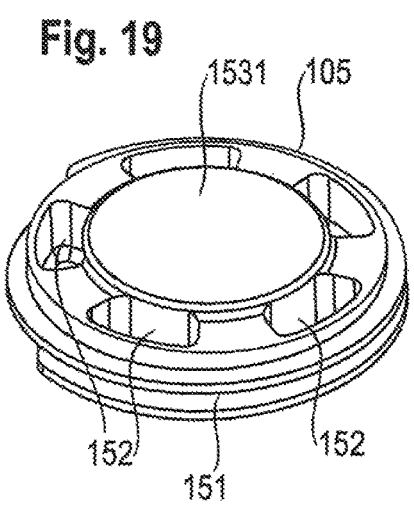
FIG. 19 shows a top perspective view of a locking device of the bone anchoring assembly according to the second embodiment.
Figure 20:
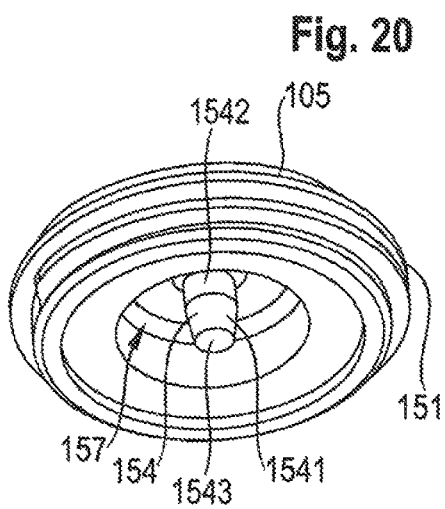
FIG. 20 shows a bottom perspective view of a locking device of the bone anchoring assembly according to the second embodiment.
Figure 21:
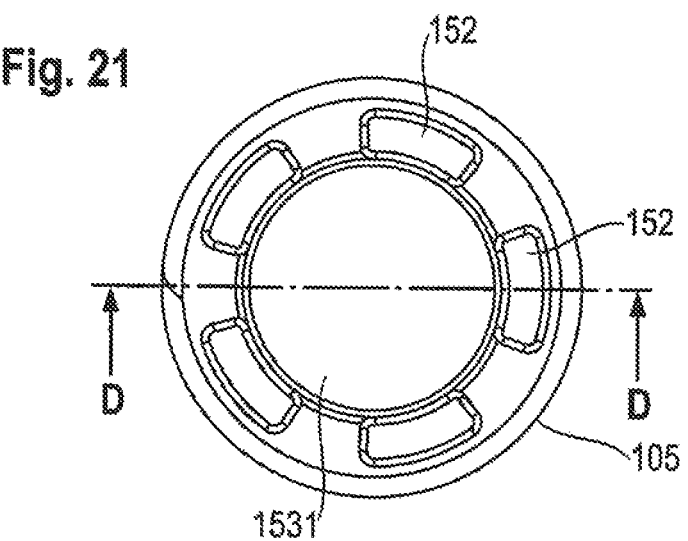
FIG. 21 shows a top view of a locking device of the bone anchoring assembly according to the second embodiment.
Figure 22:
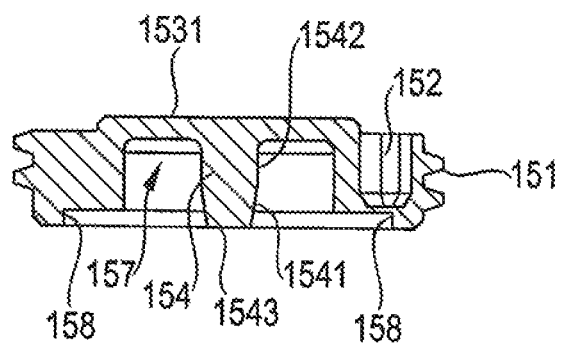
FIG. 22 shows a cross-sectional view of the locking device of the bone anchoring assembly according to the second embodiment along the line D-D shown in FIG. 21.

The locking function and operation will be explained with reference to FIGS. 14A, 14B and the steps of assembly shown in FIGS. 23 through 25. Similar to the first embodiment, the pin-shaped element 4 is inserted into insertion hole 103 via the first opening 131 such that an end portion 42 slightly protrudes from the first opening 131 above the upper planar surface 165 of the head 106.

Figure 23:
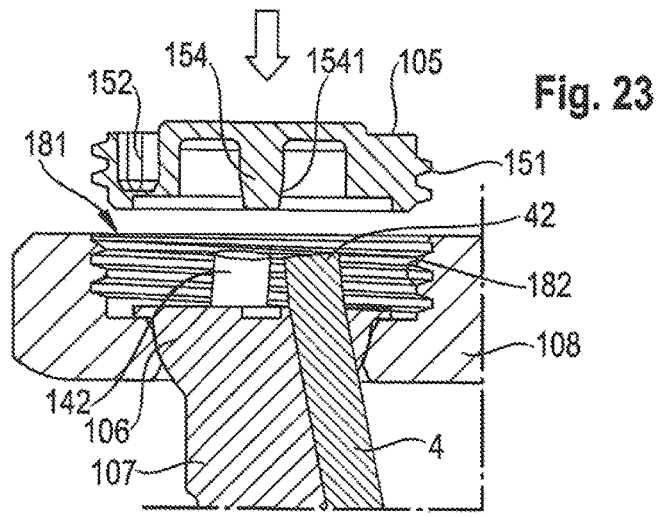
FIG. 23 shows a first step of assembling the bone anchor of the second embodiment to a bone plate.

As can be seen in FIG. 23, which shows a first step of installing the locking device 105, the main body 102 with head 106 is inserted through the aperture 181 of the bone plate 108, or into its lower recess 183, respectively, and the upper portions 42 of two pin-shaped elements 4 are shown to protrude into the bore of the aperture 181 provided by the inner thread 182.

Figure 24:
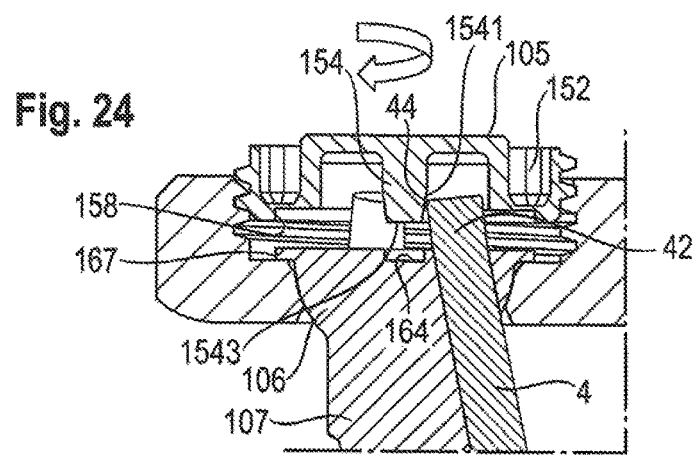
FIG. 24 shows a second step of assembling the bone anchor of the second embodiment to a bone plate.

In a next step shown in FIG. 24, using the engagement holes 152 the locking device 105 is screwed into the inner thread 182 of the aperture 181, wherein the central projection 154 rotatingly approaches the central recess 164 formed in the planar upper surface 165 of the head 106. Thereby, it also approaches the upper end portions 42 of the pin-shaped elements 4, wherein, due to its truncated cone shape of its tip, the conical wall surface 1541 laterally abuts on upper edges 44 of the respective three pin-shaped elements 4 (in the drawings, only two elements shown). Since the central projection 154 is aligned with the central longitudinal axis 121 of the bone anchor 101, the upper edges 44 of the pin-shaped elements 4 are substantially contacted simultaneously.

Figure 25:
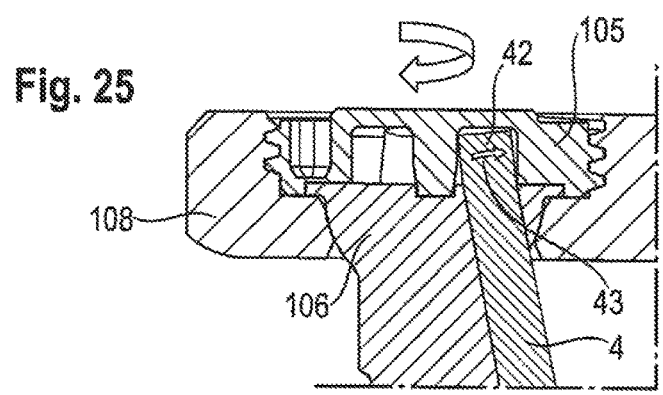
FIG. 25 shows a third step of assembling the bone anchor of the second embodiment to a bone plate.

Upon further screwing in the locking device 105, as shown in the next step displayed in FIG. 25, the end portions 42 start bending 43 laterally outwards around bending point 41 (see FIG. 14B), which represents an edge of the first opening 131. As a consequence, the pin-shaped element 4 is clamped within the insertion hole 103 and cannot move along its axial direction. Still further, an upward movement is impeded by the planar upper wall surface 1531 of the locking device 105.

A further advantage of the first and second embodiments can be found in that only a small end portion 42 of the pin-shaped element 4 is used to effect bending and thus locking, wherein a space needed for the protruding end portion 42 may be kept small and retained within a recess 57, 157 of the locking device 5, 105. In case of the first embodiment, the space needed for the protruding end portion 42 may be kept within the engagement portion 62 of the head 6, and in the second embodiment, the end portion 42 may be kept within an upper portion of the aperture 181 of the bone plate 108.

Moreover, in both embodiments, fewer parts are needed to effect locking of the pin-shaped elements 4, because the pin-shaped central projection 54, 154 may be formed monolithically with the locking device 105. Moreover, the same central projection 54, 154 may simultaneously effect bending of all end portions of pin-shaped elements 4 involved in the bone anchor 1, 101.

A third embodiment will be explained with reference to FIGS. 26 through 30. The third embodiment (and also the fourth and fifth embodiments) differs inter alia from the second embodiment in that a bone plate 208 is combined with a polyaxial bone anchor 201 instead of with a monoaxial bone anchor 101. Further differences become apparent with respect to the locking mechanism as will be described below.

Figure 26:
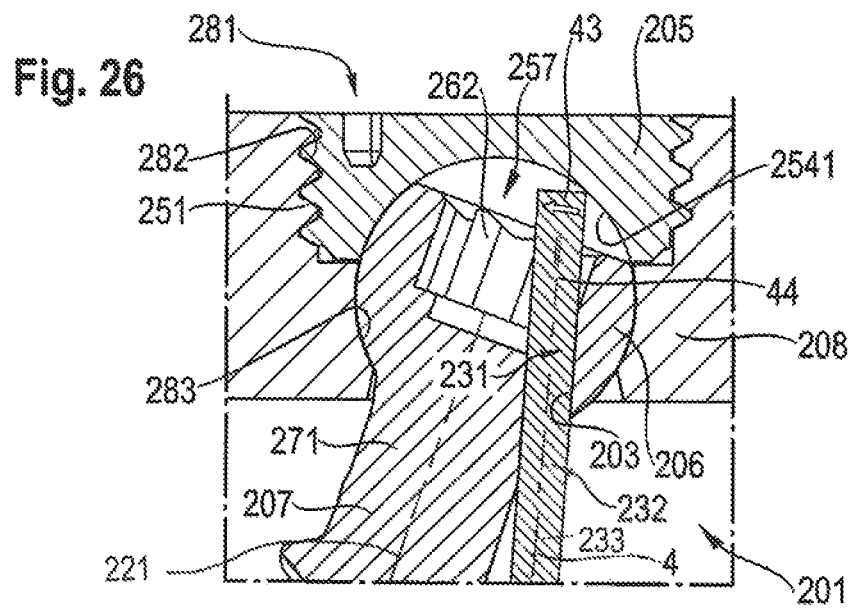
FIG. 26 shows a cross-sectional profile of a bone anchoring assembly according to a third embodiment with a bone anchor assembled to a bone plate.
Figure 27:
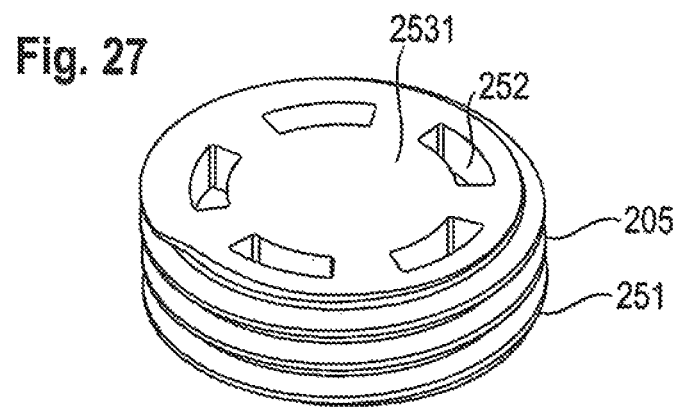
FIG. 27 shows a top perspective view of a locking device of the bone anchor of the third embodiment.
Figure 28:
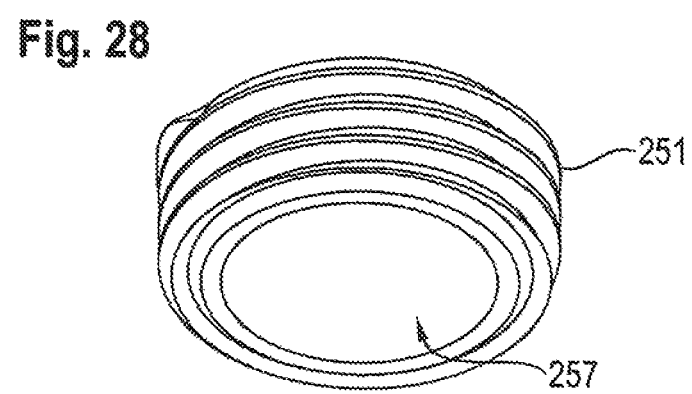
FIG. 28 shows a bottom perspective view of the locking device of the bone anchor according to the third embodiment.
Figure 29:
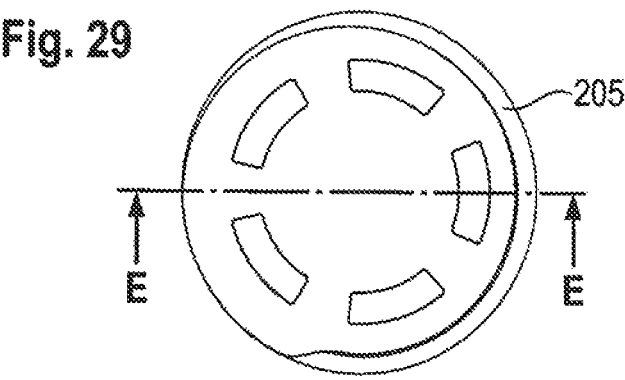
FIG. 29 shows a top view of a locking device of the bone anchor according to the third embodiment.
Figure 30:
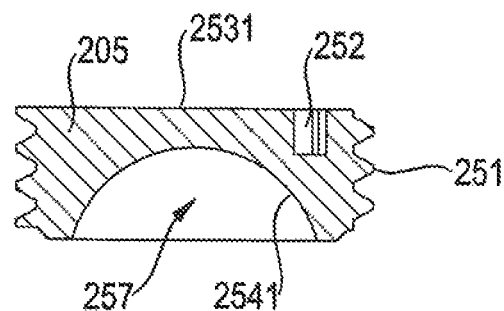
FIG. 30 shows a cross-sectional view of the locking device of the bone anchor according to the third embodiment along the line E-E shown in FIG. 29.
Figure 31:
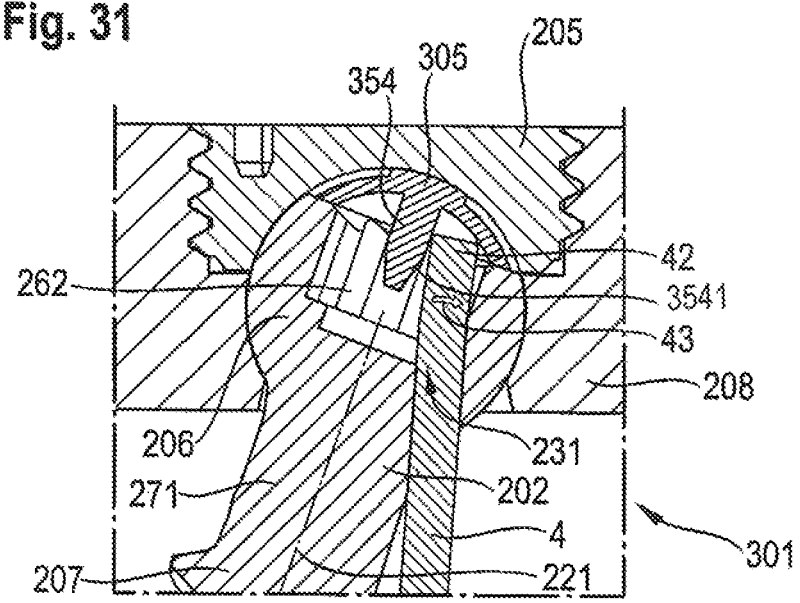
FIG. 31 shows a cross-sectional view of a bone anchoring assembly according to a fourth embodiment with a bone anchor assembled to a bone plate.
Figure 38:
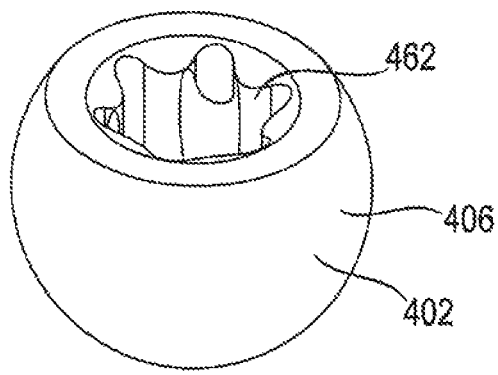
FIG. 38 shows a top perspective view of a head of the bone anchoring assembly according to the fifth embodiment.
Figure 39:
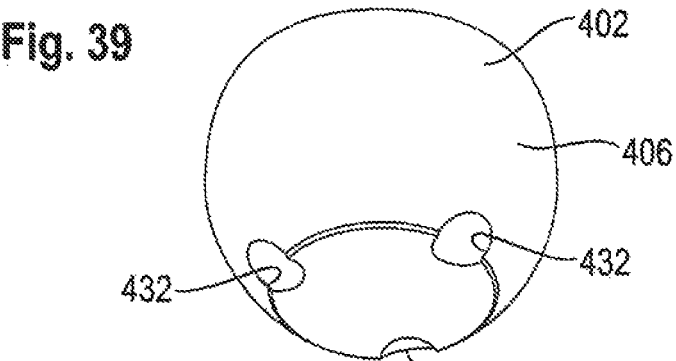
FIG. 39 shows a bottom perspective view of the head of the bone anchoring assembly according to the fifth embodiment.

As becomes apparent from FIG. 26, the bone anchor 201 comprises a spherical segment-shaped head 206 and a shank 207 having a neck portion 271. The spherical segment-shaped head 206 may be provided in a corresponding spherical segment-shaped recess 283 provided in the aperture 281 of the bone plate 208. Like in the first embodiment, the head 206 includes an engagement portion 262 for engagement by an external tool (not shown) for screwing in the bone anchor 201 into an adjacent bone material.

Similar to the first embodiment, the engagement portion 262 may be of the star (e.g., Torx) screw drive type. One, two, three or more insertion holes 203 (in FIG. 26 only one insertion hole is shown) extend from respectively recessed portions of the exemplary star (e.g., Torx) pattern at the bottom of the engagement portion 262 via a first opening 231 towards the neck portion 271, such that the inserted pin-shaped element 4 is inclined with respect to a longitudinal axis of the bone anchor 201.

The aperture 281 of the bone plate 208 is similar to that of the second embodiment wherein a bore having an inner thread 282 is provided in an upper portion thereof. A locking device as shown in FIGS. 27 through 30 is screwed into the thread 282 to fasten the head 206 of the bone anchor 201. The locking device 205 has engagement holes 252 for engagement by an external tool to screw-in the locking device 205. The external thread 251 cooperates with the inner thread 282 of the aperture 281 to effect fastening. The locking device 205 has a planar upper wall surface 2531 which is configured to be flush with the upper surface of the bone plate 208, when the head 206 is fastened.

At the bottom side of the locking device 205, an inner recess 257 is formed having a hollow spherical shape with an inner wall surface 2541. As can be seen in FIG. 26, the inner wall surface 2541 is inclined with respect to an axis 233 of the insertion hole 203, such that when the free end portion 44 of the pin-shaped element 4 abuts on the inner wall surface 2541 of the locking device 205 upon screwing-in, a lateral bending 43 towards the central longitudinal axis 221 is forced by the wall surface 2541. As a result thereof, the pin-shaped element 4 is clamped in the head 206 of the bone anchor 201 when the bone anchor is fastened by the locking device 205.

Moreover, the locking device 205 by virtue of its inner wall surface 2541 impedes loosening of the pin-shaped element 4 and a corresponding upward axial movement, even if the wall surface 2541 were not inclined.

A fourth embodiment, or a modification of the third embodiment, is shown in FIGS. 31 through 35. Same parts and features are denoted with the same reference numerals, and repeated explanation shall be avoided herein.

The fourth embodiment differs from the third embodiment in that an additional cap 305 is provided, which functions as the locking device in conjunction with the device 205. It is thus an example of a multi-part locking device. The additional cap has a top surface 3581 as shown in FIG. 32, which is spherical segment shaped corresponding to the spherically shaped inner recess 257 of device 205. The curvature of the spherical segment shaped head 206, the top surface 3581, and the inner wall surface 2541 of the inner recess 257 correspond to each other to effect pivoting of the bone anchor 201, 301 prior to final fixation within recesses 283 and 257.

The additional cap has a bell-shaped wall 3582 forming an inner recess 357 at a bottom side thereof, as can be seen in FIG. 33. As in the first and second embodiments, a pin-shaped central projection 354 is formed comprising a cylindrical base portion 3542 and a wall surface 3541 having a conical shape and a flat surface 3543 at its tip to yield a truncated cone. The bell-shaped wall 3582 is arranged to be attached to a flat upper surface of the head 206 by virtue of a lower annular surface 3583 of the bell-shaped wall 3582 such that the central projection 354 is aligned with a longitudinal axis of the main body 202 of the bone anchor 301.

In use, the main body 202 of the bone anchor 301 is first inserted into the aperture 281 and received in the recess 283. Then, the one or more pin-shaped elements 4 are inserted through respective insertion holes 203 such that a free end portion 44 protrudes from first openings 231 within the engagement portion 262 of the head 206. Thereafter, the additional cap 254 is attached to the upper planar surface of the head 206 such as to align the central projection 354 with a longitudinal axis 221 of the main body 202. Thereby, the central projection 354 is inserted between the upper edges 44 of the one or more free end portions 42 of the pin-shaped elements 4. Device 205 is screwed into the thread 282 of the aperture 281, wherein the additional cap 305 is thereby further pressed into position with central projection 354 advancing between the free end portions 42 of the pin-shaped elements 4. Thereby free end portions 42 are laterally bent 43 as described with respect to the previous embodiments. During further screwing-in of the device 205, the position of the additional cap 305 is self-adjusting due to the central projection 354.

As a consequence of this structure, clamping of the pin-shaped elements 4 and fastening of the bone anchor 301 is performed simultaneously. As in the previous embodiments, fewer parts are needed to clamp and fasten the pin-shaped elements 4 and the bone anchor 301.

A fifth embodiment will be explained with reference to FIGS. 36 through 41. The same parts and features as in the previous embodiments will be denoted with the same reference numerals and repeated explanation of those will be omitted herein. The fifth embodiment differs from the third and fourth embodiments in that a bone anchor 401 according to the fifth embodiment does not comprise a shank. Rather, a head 406 is provided as the only constituent part of a main body 402 having the function to support and anchor pin-shaped elements 4 within the adjacent bone material. As in the fourth embodiment, an additional cap 305 may be provided which provides the bending 43 and clamping mechanism, and according to an embodiment, no substantial differences are present in this regard.

FIGS. 38 through 41 reveal the overall structure of the head 406. As can be seen particularly from FIGS. 39 and 41, the main difference with respect to the fourth embodiment is found in that second openings 432 of insertion holes 403 open in a lower portion of the head 406 instead of in a transition region between the head and a neck portion of the main body.

Figure 40:
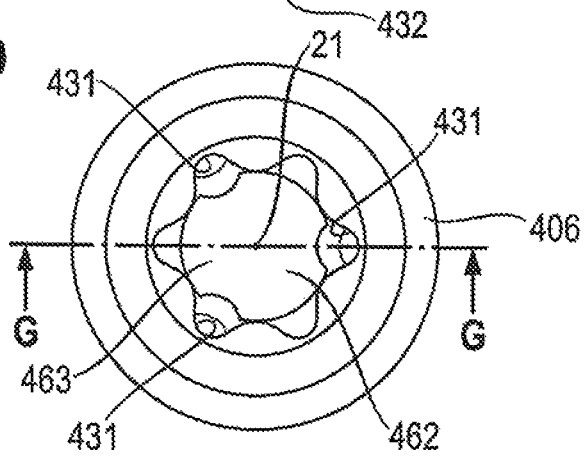
FIG. 40 shows a top view of the head of the bone anchoring assembly according to the fifth embodiment.
Figure 41:
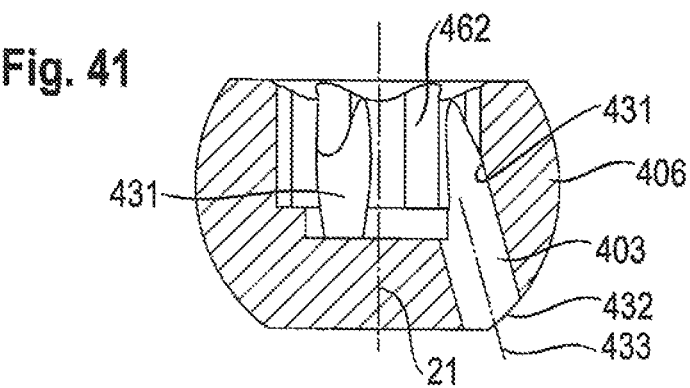
FIG. 41 shows a cross-sectional view of the head of the bone anchoring assembly according to the fifth embodiment along the line G-G shown in FIG. 40.

On the other hand, regarding FIG. 40, the structure of the head 406 seen from the top is almost identical to that of the two previous embodiments, wherein a star-shaped (e.g., Torx-shaped) engagement portion 462 has a bottom face 463 and six lateral recesses, at the bottom of three of which are provided first openings 431 of the insertion holes 403. The inclination of an axis 433 of each of the insertion holes 403 with respect to the longitudinal axis 21 of the main body 402, or head 406, is similar to the previous embodiments. Due to the omission of a shank, the inclination angles of the insertion holes 403 with respect to the longitudinal axis 21 of the main body can be chosen arbitrarily small.

In a further embodiment not shown, the head 406 of the fifth embodiment can be modified in that an engagement means may be provided at a bottom portion of the head 406 such as to attach a shank as a separate piece to the head 406. The engagement means may be a thread, a clip mechanism, a press or friction fit connection or any other mechanism.

In the embodiments above, regarding the materials selected for the bone anchors, both the locking devices and the constituent parts of the main bodies may be selected from biocompatible materials such as stainless steel, titanium, nickel titanium alloys, nitinol, or other suitable metals. Also PEEK or other suitable plastic materials may be chosen. It is not necessary that these parts are made from the same material.

While the embodiments above have been described with respect to specific parts and features, the person skilled in the art may readily conceive that the modifications of the same are also comprised by the scope of the appended claims.

Figure 42A:
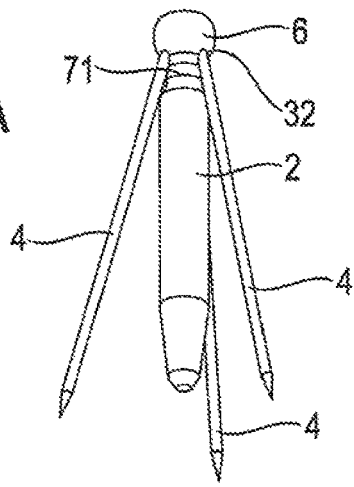
FIG. 42A shows a perspective view of a modification of the bone anchor according to the invention.
Figure 42B:
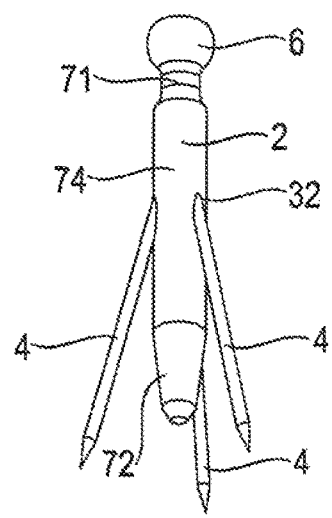
FIG. 42B shows a perspective view of a further modification of the bone anchor according to the invention.
Figure 42C:
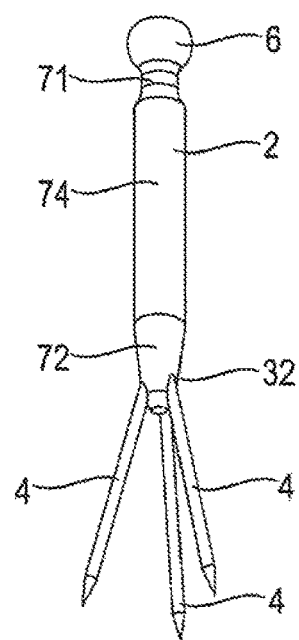
FIG. 42C shows a perspective view of a further modification of the bone anchor according to the invention.

For example, in each of the above embodiments, it is shown and described that insertion holes are provided in the head of a bone anchor, or in the head and neck portion of a bone anchor. However, as becomes apparent from FIGS. 42A through 42C, such insertion holes may also extend from the head through the shank, such that second openings 32 may be provided in a central portion of the shank 7, or even in a tip portion of the shank 7.

While the above embodiments have been described in conjunction with distinguishable heads of main bodies, a modification may also be readily conceived that the head merely represents a proximal end portion of a shank. Also, any shape of heads such as cubic, box-shaped, rounded, cylindrical, irregular etc. is encompassed by embodiments of the present invention. The head may also be plate-shaped, or a plate.

While the above embodiments have only been described in conjunction with solid main bodies of bone anchors, modifications are also encompassed in which a longitudinal channel passes through the shank and/or head.

While the first embodiment is described with a threadless shank and the second to fourth embodiments are described with threaded shanks, the reverse cases are possible as well. Also, multiple threads or interrupted threads, or an arrangement of barb elements is possible. Further, any kind of shank of a bone anchor is encompassed by the claimed subject matter, be it cylindrically shaped, tapered, conical or split.

While the above first and second embodiments have been described with a surface provided at a pin-like central projection provided at the locking device, which are inclined with respect to a longitudinal axis of the insertion hole for receiving the pin-shaped element, modifications in which a proximal end of the pin-shaped element is bent when the locking device is attached to the head of the main body of the bone anchor may also be contemplated.

According to one such modification of the second embodiment, which is shown in FIGS. 43A and 43B, a locking device 505 is provided, wherein instead of the central projection 154 of the second embodiment, an inner recess 557 without a protrusion is arranged. According to the modification, the structure of the main body 102 of bone anchor 101 as shown in FIGS. 13 and 15 through 18 is maintained and details will thus not be repeated herein. Also, as in the second embodiment, the locking device 505 maintains a planar upper surface 5531, an outer thread 551 and an annular edge 558 corresponding to annular edge 158 configured to receive annular rim 167 of bone anchor 101. However, the inner recess 557 is a chamfered wall surface 5541, which is inclined with respect to a longitudinal axis of the insertion hole 103 for receiving the pin-shaped element 4. Hence, according to the modification, a proximal end portion of the pin-shaped element 4 is bent towards a central axis of the main body 102 of bone anchor 101 when all parts are assembled. In this modification, it is not necessary, although shown in FIG. 43A, that wall surface 5541 is axially symmetric. It is possible that wall surface 5541 refers only to a projection portion of the annular outer wall of inner recess 557 wherein a ramp is provided at the outer wall to allow smoothly bending the pin-shaped elements 4.

According to a second modification of the second embodiment, which is shown in FIGS. 44A and 44B, a locking device 605 is provided, wherein instead of the central projection 154 of the second embodiment, an inner recess 657 without a central protrusion is arranged. Again, the structure of the main body 102 of bone anchor 101 as shown in FIGS. 13 and 15 through 18 is maintained and details will thus not be repeated herein. Also, as in the second embodiment, the locking device 605 maintains a planar upper surface 6531, an outer thread 651 and an annular edge 658 corresponding to annular edge 158 configured to receive annular rim 167 of bone anchor 101. However, in a top section of the inner recess 657, a rib-like structure, cogging or toothing 654 is provided either as multiple projections from the planar top surface or as multiple recesses provided therein. Each rib, cog or tooth includes a wall surface 6541 which repeatedly traverses from a lateral and clockwise or counterclockwise direction an axis of the insertion hole 103, and, when the locking device 605 is attached and screwed onto the head of main body 102, eventually enters a state in which a proximal end portion of a pin-shaped element 4 projecting from insertion hole 103 is engaged, thereby bending and locking the same. The wall surfaces 6541 thereby need not be inclined with respect to the longitudinal axis of the insertion hole 103, although an inclination is shown in the FIG. 44A. In this modification, the proximal end portions of pin-shaped elements 4 are bent in a clockwise or counterclockwise direction with respect to a central axis of the main body 102.

According to a third modification of the second embodiment, which is shown in FIGS. 45A through 45C, a locking device 705 is provided, wherein instead of the central projection 154 of the second embodiment, an inner recess 757 without a central protrusion is arranged. Again, the structure of the main body 102 of bone anchor 101 as shown in FIGS. 13 and 15 through 18 is maintained and details will thus not be repeated herein. Also, as in the second embodiment, the locking device 705 maintains a planar upper surface 7531, an outer thread 751 and an annular edge 758 corresponding to annular edge 158 configured to receive annular rim 167 of bone anchor 101. However, a ramp 754 is provided which gives rise to a slightly inclined wall surface 7541 at a top section of inner recess 757. As in the second modification of the second embodiment, the ramp 754 repeatedly traverses from a lateral and clockwise or counterclockwise direction an axis of the insertion hole 103 during each turn, and, when the locking device 705 is attached and screwed onto the head of main body 102, eventually enters a state in which a proximal end portion of a pin-shaped element 4 projecting from insertion hole 103 is engaged, thereby bending and locking the same. Also in this modification, the proximal end portions of pin-shaped elements 4 are bent in a clockwise or counterclockwise direction with respect to a central axis of the main body 102.

What is claimed is:

1. A bone anchor comprising:
   a main body defining a longitudinal axis and comprising a head at a first end of the main body, a shank extending to an opposite second end of the main body and having a first portion having a reduced outer width relative to a maximum width of the head measured perpendicular to the longitudinal axis, a neck portion positioned between the head and the shank and having a reduced outer width relative to the maximum width of the head and a maximum width of the shank measured perpendicular to the longitudinal axis, and at least one insertion hole forming an opening in the first portion of the shank, wherein the at least one insertion hole has an axis that is inclined at an angle with respect to the longitudinal axis of the main body; and
   a separate pin-shaped element configured to be received and guided within the at least one insertion hole such that the pin-shaped element protrudes outwards from the shank for anchoring the bone anchor to a bone or bone fragment.

2. The bone anchor according to claim 1, further comprising a locking device engageable with the head of the main body to fix a position of the pin-shaped element in an axial direction when the pin-shaped element is received within the at least one insertion hole.

3. The bone anchor according to claim 2, wherein the head comprises a first thread, and the locking device comprises a second thread configured to cooperate with the first thread to attach the locking device to the head.

4. The bone anchor according to claim 2, wherein the locking device comprises a recess or projection configured to contact the pin-shaped element to fix the position of the pin-shaped element in the axial direction.

5. The bone anchor according to claim 4, wherein the recess or projection of the locking device comprises a projection, and wherein the projection includes a tapered shape, a spherical segment shape, a conical shape, or a truncated cone shape.

6. The bone anchor according to claim 4, wherein the recess or projection of the locking device comprises a recess, and wherein the recess includes a threaded portion.

7. The bone anchor according to claim 4, wherein the recess or projection of the locking device comprises a recess, and wherein the recess includes a hollow tapered shape, a spherical segment shape, a conical shape, or a truncated cone shape.

8. The bone anchor according to claim 4, wherein the at least one insertion hole includes two or more insertion holes, said insertion holes forming a plurality of spaced apart openings in the shank, wherein said recess or projection comprises a surface, or a plurality of surfaces, configured to simultaneously bend respective portions of respective pin-shaped elements protruding from the respective insertion holes when the locking device is attached to the head.

9. The bone anchor according to claim 2, wherein the locking device comprises a recess or projection comprising a tapered end, on which a surface configured to contact the pin-shaped element is formed.

10. The bone anchor according to claim 1, wherein the head includes a spherical segment shape having at least a portion directed towards the shank for adjusting an angular position of the bone anchor relative to a head receiving part.

11. The bone anchor according to claim 1, wherein the at least one insertion hole is positioned closer to the second end of the main body than to the first end of the main body.

12. The bone anchor according to claim 1, wherein the shank comprises a narrowing tip at the second end of the main body, and wherein the opening in the shank is positioned at the tip.

13. The bone anchor according to claim 1, wherein the at least one insertion hole includes a plurality of insertion holes forming a plurality of spaced apart openings in the shank, and a plurality of separate pin-shaped elements configured to be received and guided within the respective plurality of insertion holes.

14. The bone anchor according to claim 1, wherein the shank comprises a bone engagement structure, and the at least one insertion hole forms an opening in a first region of the shank on which the bone engagement structure is formed.

15. The bone anchor according to claim 14, wherein the at least one insertion hole includes a plurality of insertion holes forming a plurality of spaced apart openings in the first region of the shank, and wherein the bone anchor further comprises a plurality of separate pin-shaped elements configured to be received and guided within the respective plurality of insertion holes.

16. The bone anchor according to claim 1, wherein the at least one insertion hole extends from at least one of the head and the neck and through the shank, forming an opposite opening in the head or the neck.

17. The bone anchor according to claim 1, wherein the maximum width of the entire shank is less than the maximum width of the head measured perpendicular to the longitudinal axis and prior to anchoring to a bone or bone fragment.

18. The bone anchor according to claim 1, wherein the axis of the at least one insertion hole intersects the longitudinal axis of the main body.

19. A bone anchor comprising:
a main body defining a longitudinal axis and comprising a head and at least one insertion hole, which extends from a first opening formed in the head to a second opening formed in the main body, the at least one insertion hole having an axis which is arranged to be inclined with respect to the longitudinal axis of the main body at an angle, and wherein the at least one insertion hole is configured to receive and guide therethrough a pin-shaped element to be anchored within a bone or a bone fragment; and
a locking device attachable to the main body to fix a position of the pin-shaped element in an axial direction when the pin-shaped element is received within the at least one insertion hole, the locking device comprising a recess and a projection extending in the recess along the longitudinal axis when the locking device is attached to the main body, the projection comprising a surface, wherein the axis of the at least one insertion hole extends toward the surface when the locking device is attached to the main body, such that the surface is configured to contact a portion of the pin-shaped element protruding from the first opening when the pin-shaped element is received within the at least one insertion hole;
wherein the locking device is formed as a cap configured to be attached to the head, whereby, when the locking device is attached to the head, the surface of the locking device is configured to prevent the pin-shaped element from moving along the axis of the at least one insertion hole, and
wherein the head has a spherical segment shape.

20. A bone anchor comprising:
a main body defining a longitudinal axis and comprising a head and at least one insertion hole, which extends from a first opening formed in the head to a second opening formed in the main body, the at least one insertion hole having an axis which is arranged to be inclined with respect to the longitudinal axis of the main body at an angle, and wherein the at least one insertion hole is configured to receive and guide therethrough a pin-shaped element to be anchored within a bone or a bone fragment; and
a locking device attachable to the main body to fix a position of the pin-shaped element in an axial direction when the pin-shaped element is received within the at least one insertion hole, the locking device comprising a recess and a projection extending in the recess along the longitudinal axis when the locking device is attached to the main body, the projection comprising a surface, wherein the axis of the at least one insertion hole extends toward the surface when the locking device is attached to the main body, such that the surface is configured to contact a portion of the pin-shaped element protruding from the first opening when the pin-shaped element is received within the at least one insertion hole;
wherein the locking device is formed as a cap configured to be attached to the head, whereby, when the locking device is attached to the head, the surface of the locking device is configured to prevent the pin-shaped element from moving along the axis of the at least one insertion hole, and
wherein the projection comprises a tapered end, on which the surface is formed.

21. A bone anchor comprising:
a main body defining a longitudinal axis and comprising a head at a first end of the main body, a shank extending to an opposite second end of the main body, a neck portion positioned between the head and the shank and having a reduced outer width relative to a maximum width of the head and a maximum width of the shank each measured perpendicular to the longitudinal axis, and at least one insertion hole forming an opening in the shank, wherein the at least one insertion hole has an axis that is inclined at an angle with respect to the longitudinal axis of the main body, and wherein the axis of the at least one insertion hole intersects the longitudinal axis of the main body; and
a separate pin-shaped element separable from the head of the main body and configured to be received and guided within the at least one insertion hole such that the pin-shaped element protrudes outwards from the shank for anchoring the bone anchor to a bone or bone fragment.

22. The bone anchor according to claim 21, wherein the axis of the at least one insertion hole intersects the longitudinal axis of the main body at a position external to the main body.

* * * * *

UNITED STATES PATENT AND TRADEMARK OFFICE
CERTIFICATE OF CORRECTION

PATENT NO. : 10,258,397 B2  
APPLICATION NO. : 15/888813  
DATED : April 16, 2019  
INVENTOR(S) : Lutz Biedermann et al.

Page 1 of 1

It is certified that error appears in the above-identified patent and that said Letters Patent is hereby corrected as shown below:

In the Specification

Column 6, Line 37    delete "a" and insert -- α --

Column 6, Line 38    delete "a" and insert -- α --

Column 6, Line 48    delete "a" and insert -- α --

Signed and Sealed this  
Tenth Day of March, 2020

Andrei Iancu  
*Director of the United States Patent and Trademark Office*